United States Patent

Yoshikawa et al.

[11] Patent Number: 5,449,826
[45] Date of Patent: Sep. 12, 1995

[54] 5-AMINO-2-PHENOXYSULFONANILIDE COMPOUND

[75] Inventors: Kensei Yoshikawa; Shuji Saito; Yohichi Shimazaki; Mariko Kashiwa; Katsuo Hatayama, all of Tokyo, Japan

[73] Assignee: Taisho Pharmaceutical Co., Ltd., Japan

[21] Appl. No.: 351,341

[22] PCT Filed: Apr. 21, 1993

[86] PCT No.: PCT/JP93/00518
    § 371 Date: Dec. 9, 1994
    § 102(e) Date: Dec. 9, 1994

[87] PCT Pub. No.: WO93/25520
    PCT Pub. Date: Dec. 23, 1993

[30] Foreign Application Priority Data

Jun. 12, 1992 [JP]  Japan .................. 4-152554

[51] Int. Cl.$^6$ .......................... C07C 211/45
[52] U.S. Cl. ............................... 564/99
[58] Field of Search ............ 564/99; 514/605

[56] References Cited

U.S. PATENT DOCUMENTS

| | | | |
|---|---|---|---|
| 3,531,552 | 9/1970 | Nelson et al. | 260/556 |
| 3,840,597 | 10/1974 | Moore et al. | 260/556 F |
| 3,856,859 | 12/1974 | Moore | 260/556 |
| 4,866,091 | 9/1989 | Matsuo | 514/471 |
| 4,885,367 | 12/1989 | Yoshikawa et al. | 546/216 |
| 5,374,764 | 12/1994 | Yoshikawa et al. | 560/13 |

FOREIGN PATENT DOCUMENTS

| | | |
|---|---|---|
| 63-190869 | 8/1988 | Japan . |
| 2268 | 1/1990 | Japan . |
| 222260 | 1/1990 | Japan . |
| 2300122 | 12/1990 | Japan . |

Primary Examiner—Glennon H. Hollrah
Assistant Examiner—Brian M. Burn
Attorney, Agent, or Firm—Lorusso & Loud

[57] ABSTRACT

To provide an excellent compound having anti-inflammatory, antipyretic, analgesic and antirheumatic actions.

A 5-amino-2-phenoxysulfonanilide compound represented by the formula:

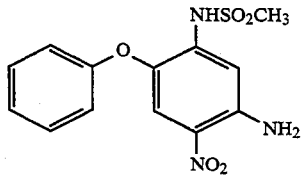

and the salts thereof have potent anti-inflammatory, antipyretic, analgesic and antirheumatic actions, and therefore they are useful as anti-inflammatory, antipyretic, analgesic and antirheumatic agents.

1 Claim, No Drawings

5-AMINO-2-PHENOXYSULFONANILIDE COMPOUND

This application is a 371 of PCT/JP93/00518, filed Apr. 21, 1993.

INDUSTRIAL FIELD

The present invention relates to a 5-amino-2-phenoxysulfonanilide compound having anti-inflammatory, antipyretic, analgesic and antirheumatic actions.

BACKGROUND ART

Various 2-phenoxysulfonanilide compounds have been known in the past and especially the compounds described in the specification of U.S. Pat. No. 4,885,367 are considered to be the structurally close to the compound of the present invention.

However, these compounds described in the above-mentioned specification are insufficiently effective.

An object of the present invention is to provide drugs having excellent anti-inflammatory, antipyretic, analgesic and antirheumatic actions.

DISCLOSURE OF THE INVENTION

As a result of extensive researches for the purpose of solving the above-mentioned problem, the present inventors have found that a 5-amino-2-phenoxysulfonanilide compound has excellently useful anti-inflammatory action, and have accomplished the present invention.

The present invention relates to a 5-amino-2-phenoxysulfonanilide compound represented by Formula (I):

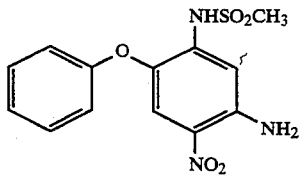

(I)

and to pharmaceutically acceptable salts thereof.

In the present invention, the salt refers to salts with alkali metals (e.g. sodium and potassium), alkaline earth metals (e.g. calcium and magnesium), ammonia and organic bases (e.g. ethanolamine, lysine and arginine).

The compound of Formula (I) of the present invention can be prepared, for example, by the following preparation steps (a) to (f).

(a) First, 2-fluoro-5-nitroaniline is reacted with methanesulfonic acid or a reactive derivative thereof (e.g. acid halides or acid anhydrides) to give a compound represented by Formula (II):

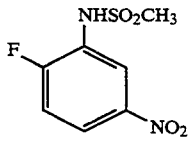

(II)

This reaction wherein the methanesulfonic acid is used is preferably carried out in the presence of a condensing agent such as N,N'-dicyclohexylcarbodiimide. In case where the reactive derivative is used, the reaction is preferably carried out in the presence of a base such as, for example, inorganic bases (e.g. lithium hydroxide, sodium hydroxide, potassium hydroxide, sodium carbonate, potassium carbonate, sodium bicarbonate or potassium bicarbonate) or organic bases (e.g. triethylamine, tri-n-butylamine, 1,5-diazabicyclo[4.3.0]-5-nonene, 1,8-diazabicyclo[5.4.0]-7-undecene, 4-methylmorpholine, 1-methylpiperidine, pyridine or N,N-dimethylaminopyridine).

This reaction is usually carried out in the presence of a solvent such as, for example, dichloromethane, chloroform, ethyl acetate, dioxane, tetrahydrofuran, ethyl ether, benzene, toluene, xylene, acetone, acetonitrile, water, pyridine, N,N-dimethylformamide or dimethyl sulfoxide.

(b) Subsequently, a compound of Formula (II) is reacted with phenol in the presence of a base to give a compound represented by Formula (III):

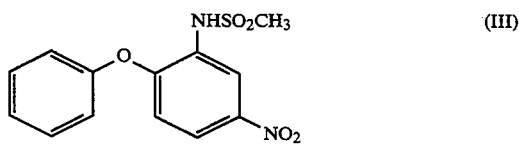

(III)

Examples of the base in the reaction are alkali metal hydroxides (e.g. lithium hydroxide, sodium hydroxide and potassium hydroxide), alkali metal carbonates (e.g. sodium carbonate and potassium carbonate), alkali metal bicarbonates (e.g. sodium bicarbonate and potassium bicarbonate), alkali metal hydrides (e.g. sodium hydride and potassium hydride), inorganic bases (e.g. metallic sodium and sodium amide) and organic bases (e.g. triethylamine, tri-n-butylamine, 1,5-diazabicyclo[4.3.0]-5-nonene, 1,8-diazabicyclo[5.4.0]-7-undecene, pyridine and N,N-dimethylaminopyridine).

This reaction may be carried out in the absence or presence of a solvent which is arbitrarily chosen from, for example, dioxane, tetrahydrofuran, ethyl ether, petroleum ether, n-hexane, cyclohexane, benzene, toluene, xylene, pyridine, N,N-dimethylformamide, dimethyl sulfoxide, dichloromethane, chloroform or water. Furthermore, the reaction can be accelerated by adding potassium iodide, tris[2-(2-methoxyethoxy)ethyl]amine, a quaternary ammonium salt (e.g. tetra-n-butylammonium chloride, benzyltriethylammonium chloride and benzyltriethylammonium bromide) or a crown ether (e.g. 18-crown-6 ether).

(c) Then, the nitro group of the compound of Formula (III) is reduced to give a compound represented by Formula (IV):

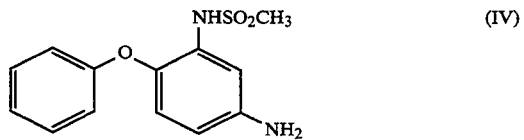

(IV)

This reaction may be a conventional reduction by which a nitro group is introduced to an amino group, for example, a catalytic reduction using palladium-carbon, Raney nickel or platinum as a catalyst, a reduction using iron or tin, a reduction using sodium sulfide-ammonium chloride, a reduction using sodium borohydride or lithium aluminium hydride.

The solvent to be used in the reaction can be arbitrarily chosen depending on the reduction. Generally, for example, alcohols (e.g. methanol, ethanol or n-propanol), water, acetic acid, ethyl acetate, dioxane, tetrahydrofuran or acetonitrile can be used as the solvent.

(d) Subsequently, the compound of Formula (IV) is reacted with a compound represented by Formula (V):

Cl—CO—R  (V)

(wherein R is an alkyl group having 1 to 5 carbon atoms, an alkoxy group having 1 to 5 carbon atoms or an alkoxycarbonyl group having 2 to 6 carbon atoms) or a compound represented by Formula (VI):

(R—CO)$_2$O  (VI)

(wherein R is an alkyl group having 1 to 5 carbon atoms, an alkoxy group having 1 to 5 carbon atoms or an alkoxycarbonyl group having 2 to 6 carbon atoms) to give a compound represented by Formula (VII):

(VII)

(wherein R is as defined above).

This reaction is preferably carried out in the presence of a base such as, for example, alkali metal hydroxides (e.g. lithium hydroxide, sodium hydroxide or potassium hydroxide), alkali metal carbonates (e.g. sodium carbonate or potassium carbonate), alkali metal bicarbonates (sodium bicarbonate or potassium bicarbonate), alkali metal hydrides (e.g. sodium hydride or potassium hydride), inorganic bases (e.g. metallic sodium or sodium amide) or organic bases (e.g. triethylamine, tri-n-butylamine, 1,5-diazabicyclo[4.3.0]-5-nonene, 1,8-diazabicyclo[5.4.0]-7-undecene, pyridine or N,N-dimethylaminopyridine).

This reaction is carried out in the absence or presence of a solvent which is arbitatrarily chosen from, for example, dioxane, tetrahydrofuran, ethyl ether, petroleum ether, n-hexane, cyclohexane, benzene, toluene, xylene, chlorobenzene, pyridine, ethyl acetate, acetonitrile, N,N-dimethylformamide, dimethyl sulfoxide, dichloromethane, chloroform or water.

(e) The compound of Formula (VII) is nitrated by a nitrating agent such as nitric acid or a nitrate to give a compound represented by Formula (VIII):

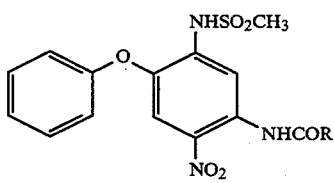

(VIII)

(wherein R is as defined above).

Examples of the nitrate to be used in the nitration are sodium nitrate, potassium nitrate, ferric nitrate and urea nitrate. The solvent to be used in the reaction is preferably arbitrarily chosen depending on the nitrating agent to be used, for example, acetic acid, acetic anhydride, trifluoroacetic acid, sulfuric acid, dichloromethane, chloroform, benzene, dioxane or ethanol.

(f) Finally, the compound of Formula (VIII) is hydrolyzed to give a compound of Formula (I) of the present invention.

The hydrolysis in this reaction may be a conventional hydrolysis of an amide under the basic or acidic condition, for example, a hydrolysis using lithium hydroxide, sodium hydroxide, potassium hydroxide, sodium carbonate, potassium carbonate, sodium methoxide, sodium ethoxide or potassium t-butoxide for the basic condition, or a hydrolysis using hydrochloric acid, hydrobromic acid or sulfuric acid for the acidic condition.

Examples of the solvent to be used in the reaction are water, methanol, ethanol, propanol, t-butanol, tetrahydrofuran, dioxane, benzene, toluene, xylene, chlorobenzene, N,N-dimethylformamide, dimethyl sulfoxide, formic acid and acetic acid, but it is preferably that the solvent is appropriately chosen depending on the condition of the hydrolysis.

The compound of the present invention can be administered orally or parenterally in the conventional dosage forms such as, for example, tablets, dusts, granules, powders, capsules, solutions, emulsions, suspensions and injections, all of which can be prepared by conventional practices. The dose used for humans as an anti-inflammatory, antipyretic, analgesic or antirheumatic agent is different depending on the age and body weight of the patient, symptoms of the disease, route of administration and frequency of administration, but it is usually from 5 to 600 mg per day.

BEST MODE FOR CARRYING OUT THE INVENTION

The present invention is illustrated in more detail by the following examples.

EXAMPLE 1

(1) To 334 ml of a pyridine solution containing 52.1 g of 2-fluoro-5-nitroaniline was added 42.1 g of methanesulfonyl chloride under ice cooling, followed by stirring at room temperature for 7 hours. Water was added to the reaction solution, the precipitate was collected by filtration, and the crude crystals were recrystallized from ethanol to give 56.9 g of N-(2-fluoro-5-nitrophenyl)methanesulfonamide as pale yellow needles.

m.p. 162.5°~163.5° C.

(2) To 250 ml of an aqueous solution containing 73.5 g of phenol and 31.2 g of sodium hydroxide was added 50.0 g of N-(2-fluoro-5-nitrophenyl)methanesulfonamide, followed by reflux for 5 hours and then ice-cooling. To the ice-cooled reaction solution were successively added 50 ml of 36% hydrochloric acid and 200 ml of ethanol with stirring. The precipitate was collected by filtration, successively washed with water and ethanol, and air-dried to give 52.2 g of N-(5-nitro-2-phenoxyphenyl)methanesulfonamide as yellow prisms.

m.p. 112°~113.5° C.

(3) To 52.1 g of N-(5-nitro-2-phenoxyphenyl)methanesulfonamide was added 51 ml of an aqueous solution containing 2.7 g of ammonium chloride, and then 42.5 g of an iron powder was added thereto with heating at 80° C. with stirring, followed by stirring for 2 hours. To the reaction cooled to 50° C. were added ethyl acetate and water, and the precipitate was filtered. After extraction with ethyl acetate, the organic layer was successively washed with water and a saturated aqueous sodium chloride solution, and dried over anhydrous magnesium sulfate. The solvent was evaporated, and the residue was recrystallized from ethanol to give 29.6 g of N-(5-amino-2-phenoxyphenyl)methanesulfonamide.

m.p. 111.5°~113.5° C.

(4) To 180 ml of a dichloromethane solution containing 13.7 g of oxalyl chloride were successively added 9.5 g of n-pentanol and 8.5 g of pyridine under ice cooling, followed by stirring for 5 minutes. To the reaction solution cooled to −78° C. was added 70 ml of a dichloromethane solution containing 20.0 g of N-(5-amino-2-phenoxyphenyl)methanesulfonamide and 8.5 g of pyridine, followed by stirring at room temperature for 10 minutes. The reaction solution, after addition of water, was extracted with dichloromethane, and the organic layer was successively washed with water, 3N hydrochloric acid and a saturated aqueous sodium chloride solution and dried over anhydrous magnesium sulfate. After evaporation of the solvent, the residue was recrystallized from ethanol to give 17.2 g of N-[5-(n-pentyl)oxalylamino-2-phenoxyphenyl]methanesulfonamide as colorless crystals.

m.p. 164°~165° C.

(5) To 60 ml of an acetic acid solution containing 17.1 g of N-[5-(n-pentyl)oxalylamino-2-phenoxyphenyl]methanesulfonamide was added 2.7 g of 60% nitric acid with heating at 90° C. with stirring, followed by stirring for 10 minutes. The reaction solution was cooled back to room temperature, and water was added thereto. The precipitate was collected by filtration and recrystallized from ethanol to give 11.5 g of N-[4-nitro-5-(n-pentyl)oxalylamino-2-phenoxyphenyl]methanesulfonamide as yellow needles.

m.p. 123.5°~125.5° C.

(6) To 25 ml of a tetrahydrofuran solution containing 2.5 g of N-[4-nitro-5-(n-pentyl)oxalylamino-2-phenoxyphenyl]methanesulfonamide was added 25 ml of 10% aqueous sodium hydroxide solution at room temperature, followed by stirring for 10 minutes. The reaction solution, after neutralization with 3N hydrochloric acid, was extracted with ethyl acetate, and the organic layer was successively washed with water and a saturated aqueous sodium chloride solution, and dried over anhydrous magnesium sulfate. After evaporation of the solvent, the residue was recrystallized from ethanol to give 1.6 g of N-(5-amino-4-nitro-2-phenoxyphenyl)methanesulfonamide as orange-colored prisms.

m.p. 175°~176° C.

EXAMPLE 2

Following a procedure similar to that of Example 1 except for the use of ethanol-n-hexane in place of ethanol for recrystallization of the residue in Example 1(6), there was obtained N-(5-amino-4-nitro-2-phenoxyphenyl)methanesulfonamide as orange-colored needles.

m.p. 164°~165° C.

INDUSTRIAL UTILIZATION

The compound which is an active ingredient in the present invention has potent anti-inflammatory, antipyretic, analgesic and antirheumatic actions with fewer side effects such as gastrointestinal disorders, and therefore it is useful as anti-inflammatory, antipyretic, analgesic or antirheumatic agents.

Experiment 1 [Carrageenin foot edema inhibition test]

A carrageenin foot edema inhibition test was carried out according to the method of Winter et al [Proc. Soc. Exp. Biol. Med., vol. 111, page 544 (1962)].

Six Wistar strain rats (for each group) were administered orally with the test drugs [the compound (a) of the present invention and the control drug (b)], each suspended in 5% aqueous gum arabic solution in an amount of 1 ml per 100 g of body weight. An hour later, 0.1 ml of 1% carrageenin was administered subcutaneously into the left hind foot pad. Three hours after administration of carrageenin, the volume of the foot was determined, and the edema inhibition rate (%) was calculated for the anti-inflammatory effect.

Dose of the test drug was 0.3 mg/kg.

Experiment 2 [Adjuvant arthritis (therapy) test]

An adjuvant arthritis (therapy) test was carried out according to the method of Winter et al [Arthritis Rheum., vol. 12, page 472 (1969)].

Seven Lewis strain rats (for each group) were administered subcutaneously 0.7% Mycobacterium tuberculosis suspended in liquid paraffin into the left hind foot pad to induce adjuvant arthritis. 15~18 Days after administration of adjuvant, rats with fully developed arthritis were administered orally with test drugs [the compound (a) of the present invention and the control compound (b)], each suspended in 5% aqueous gum arabic solution in an amount of 1 ml per 100 g of body weight once a day for 4 days.

On the day after the final administration, the volume of the foot was determined, and the edema inhibition rate (%) was calculated for the therapeutical effect. Dose of the test drug was 0.2 mg/kg.

Experiment 3 [Adjuvant arthritis (pain) test]

An adjuvant arthritis (pain) test was carried out according to the method of Katsuno et al [Chem. Pharm. Bull., vol. 23, No. 6 page 1184 (1975)].

Ten Lewis strain rats (for each group) were administered subcutaneously 0.7% Mycobacterium tuberculosis suspended in liquid paraffin into the left hind foot pad to induce adjuvant arthritis. 15~18 Days after administration of adjuvant, rats with arthritis, which had a squeaking response to the pain caused by stimulation of flexion and extension of the right hind foot pad, were administered orally with test drugs [the compound (a) of the present invention and the control compound (b)], each suspended in 5% aqueous gum arabic solution in an amount of 1 ml per 100 g of body weight. The occurrence of squeaking response was monitored with time over 5 hours after the administration, and the inhibition rate (%) was calculated to examine the analgesic effect. Dose of the test drug was 1.0 mg/kg.

Results obtained in Experiments 1 to 3 are summarized in Table 1.

TABLE 1

| Test drug | Experiment 1 | Experiment 2 | Experiment 3 |
|---|---|---|---|
| a | 31 | 43 | 45 |
| b | 20 | 21 | 14 |

The compound (a) of the present invention: the compound of Example 1.

Control compound (b): N-(4-nitro-2-phenoxyphenyl)methanesulfonamide

Experiment 4 [1L-1 formation inhibition test]

Healthy human peripheral blood heparinized was layered over Lymphoprep (Daiichi Pharmaceutical Co.) under aseptic conditions to remove red blood cell, and the cell counts were adjusted to $2 \times 10^6$ cells/ml by floating the cells in RPMI-1640 medium (Gibco Co.) containing 10% fatal bovine serum, penicillin 100 U/ml, streptomycin 100 U/ml, HEPES buffer 10 mM and L-glutamin 2 mM.

500 μl of the prepared cell floating solution, 2.0 μg of ConA (Sigma Co.) and 250 μl of the above-mentioned medium of the test drugs [the compound (a) of the present invention and the control compound (b)]were placed on a microplate (flat bottom, 24-holes, Iwaki Glass Co.), and incubated for 48 hours in a 5% $CO_2$ incubator. The test drug of the medium solution, after dissolution of the test drug in ethanol, was adjusted to 0.05% of the final concentration of ethanol by diluting with the above-mentioned medium solution. After incubation, the amount (pg/ml) of 1L-1β in the cell supernatant was determined by means of ELISA kit (Amasham Co.), and 1L-1β formation inhibition rate (%) was calculated to give the $IC_{50}$ value.

The concentrations of the test drug were 0, 3, 10 and 30 μg/ml.

As a result, $IC_{50}$ value of the 1L-1 formation inhibiting action of the compound (a) of the present invention was 13.3 μg/ml, but the control compound (b) did not show 50% or more inhibition in the above concentration, and therefore the $IC_{50}$ value could not be calculated.

We claim:

1. A compound represented by the formula:

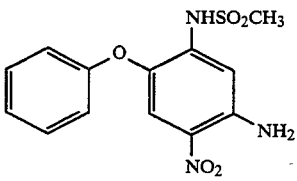

or a salt thereof.